United States Patent [19]
Best, Jr. et al.

[11] Patent Number: 5,695,475
[45] Date of Patent: Dec. 9, 1997

[54] SYRINGE APPARATUS

[76] Inventors: Lester Best, Jr., 3011-D S. Holden Rd., Greensboro, N.C. 27419; Henry Boyd, III, 3223-D Orange St., Greensboro, N.C. 27405

[21] Appl. No.: 571,452

[22] Filed: Dec. 13, 1995

[51] Int. Cl.$^6$ ................................................. A61M 5/32
[52] U.S. Cl. ................... 604/198; 604/110; 604/191; 604/205; 604/218; 128/763; 128/919
[58] Field of Search ................... 128/760, 763, 128/764–766, 912, 919; 604/115, 181, 187, 190, 191, 192, 198, 110, 218, 195, 197, 263, 200, 201, 204–206, 232, 244, 88, 82, 87, 56

[56] References Cited

U.S. PATENT DOCUMENTS

| | | |
|---|---|---|
| 2,876,770 | 3/1959 | White . |
| 3,749,084 | 7/1973 | Cucchiara ................ 604/191 |
| 4,258,713 | 3/1981 | Wardlaw . |
| 4,507,118 | 3/1985 | Dent ........................ 604/198 |
| 4,542,749 | 9/1985 | Caselgrandi et al. . |
| 4,573,976 | 3/1986 | Sampson et al. ........... 604/198 |
| 4,581,015 | 4/1986 | Alfano ...................... 604/232 |
| 4,664,654 | 5/1987 | Strauss ..................... 604/198 |
| 4,723,943 | 2/1988 | Spencer .................... 604/263 |
| 4,725,267 | 2/1988 | Vaillancourt .............. 604/192 |
| 4,747,837 | 5/1988 | Hauck ...................... 604/198 |
| 4,767,413 | 8/1988 | Haber et al. ............... 604/198 |
| 4,787,891 | 11/1988 | Levin et al. ............... 604/187 |
| 4,813,426 | 3/1989 | Haber et al. ............... 128/763 |
| 4,820,275 | 4/1989 | Haber et al. ............... 604/198 |
| 4,887,999 | 12/1989 | Alles ....................... 604/110 |
| 4,908,023 | 3/1990 | Yuen ....................... 604/118 |
| 4,909,795 | 3/1990 | Gelabert ................... 604/198 |
| 4,917,679 | 4/1990 | Kronner ................... 604/198 |
| 4,929,237 | 5/1990 | Medway ................... 604/198 |
| 4,932,947 | 6/1990 | Cardwell .................. 604/198 |
| 4,955,868 | 9/1990 | Klein ....................... 604/263 |
| 4,958,622 | 9/1990 | Selenke ................... 604/192 |
| 5,024,616 | 6/1991 | Ogle, II ................... 128/919 |
| 5,265,621 | 11/1993 | Simpson et al. .......... 128/764 |
| 5,360,409 | 11/1994 | Boyd, III et al. ........ 604/198 |
| 5,376,080 | 12/1994 | Petrussa .................. 604/198 |
| 5,389,070 | 2/1995 | Morell .................... 604/183 |

*Primary Examiner*—Corrine M. McDermott
*Assistant Examiner*—Ronald K. Stright, Jr.

[57] ABSTRACT

Syringe apparatus is provided which can be used in multiple ways such as injecting patients with various medications, taking blood samples, or in IV (intravenous) applications. The apparatus includes an outer sleeve slidably positioned over an inner sleeve which includes a penetrable member thereon. The penetrable member allows needle injection of a fluid from another syringe into the inner sleeve. One embodiment of the apparatus has a single pointed needle attached to the inner sleeve and a second embodiment has a double pointed needle for use in blood collection or the like. The syringe apparatus has a built-in safety feature by the use of a coiled spring which causes the needle to retract within the outer sleeve when released to prevent accidental needle puncture.

11 Claims, 4 Drawing Sheets

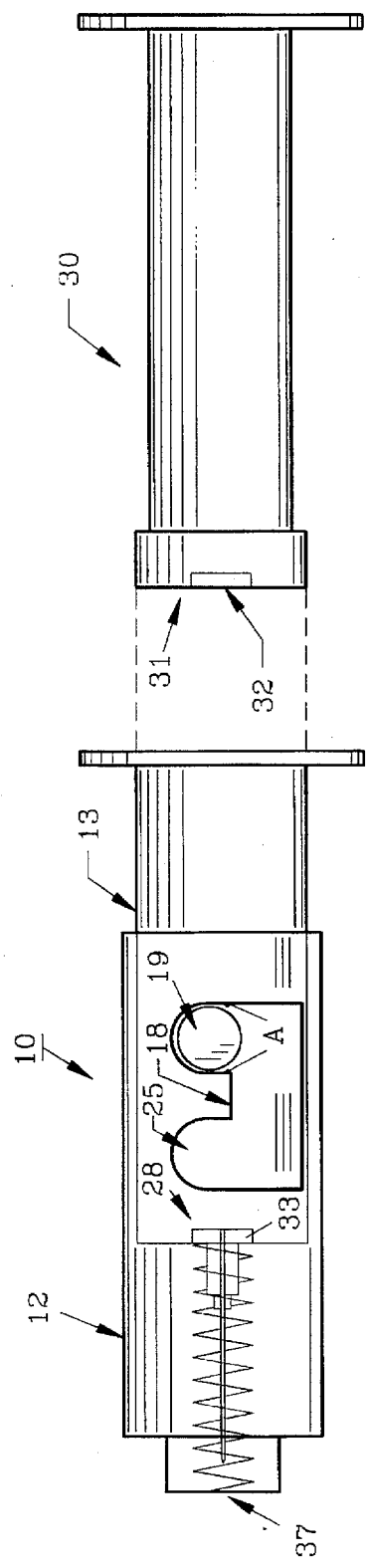
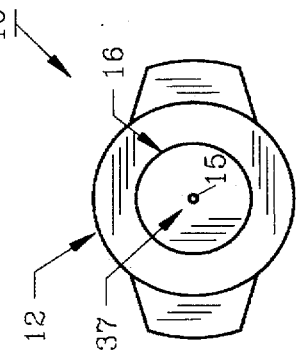
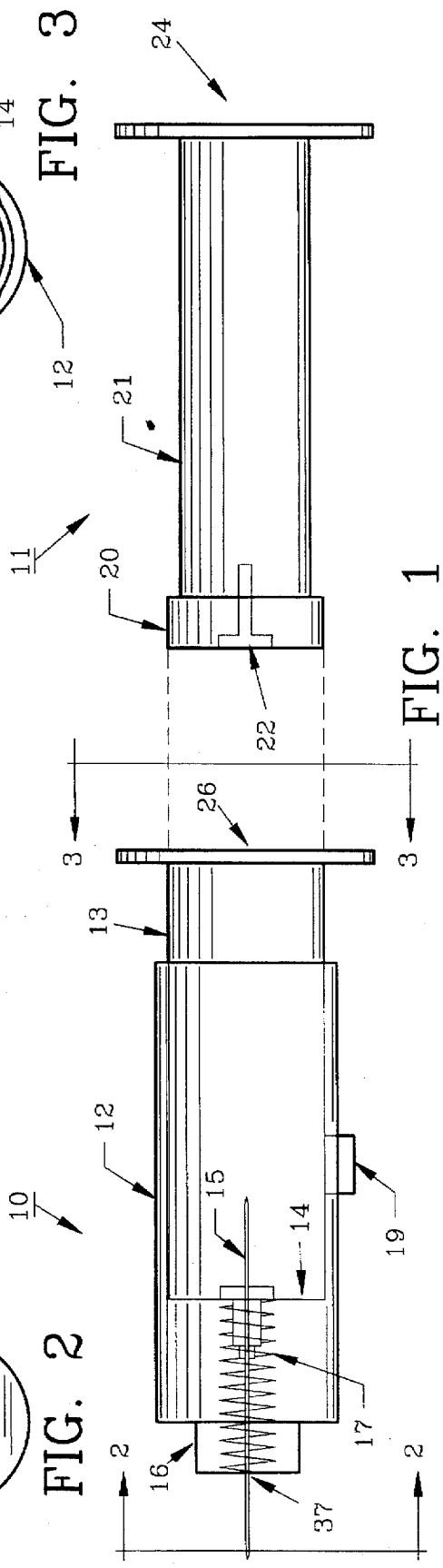
FIG. 1 FIG. 2 FIG. 3 FIG. 4

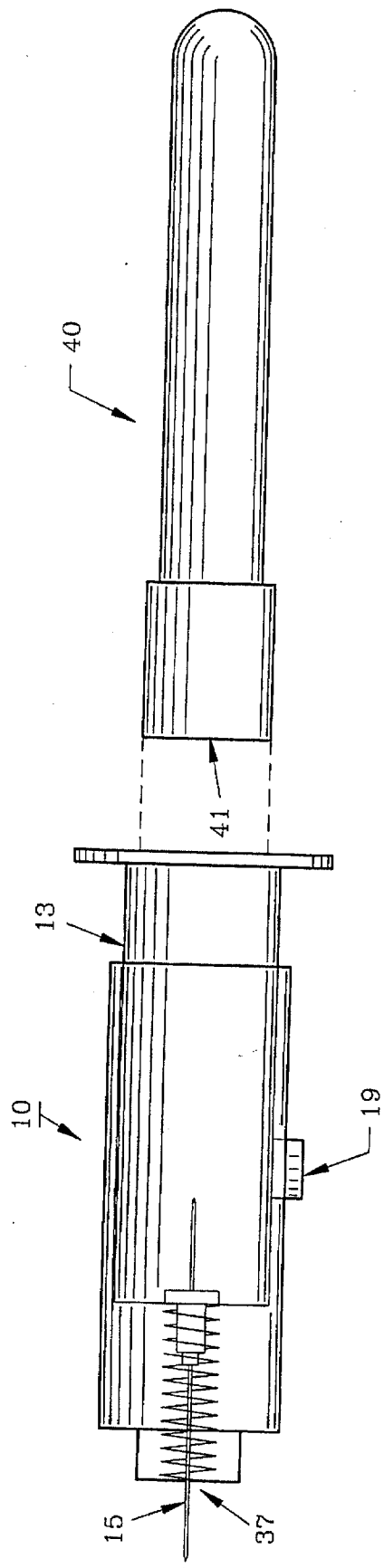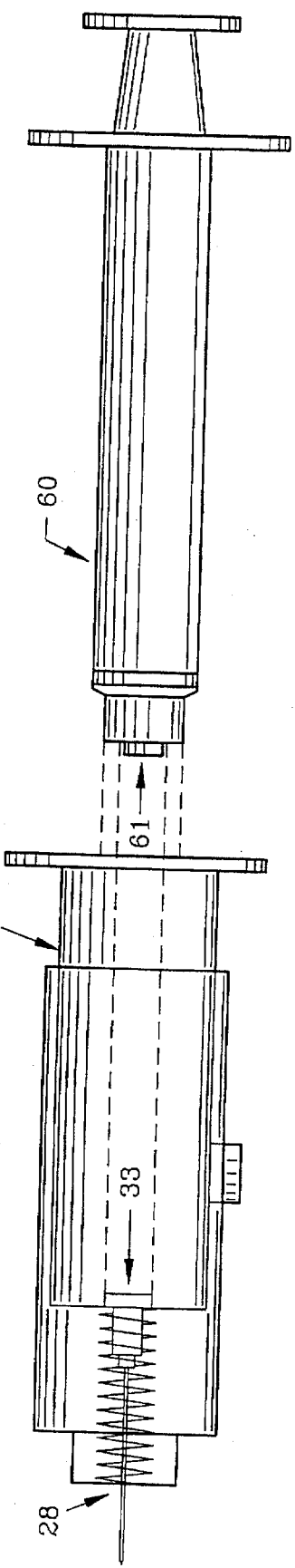
FIG. 5
FIG. 6

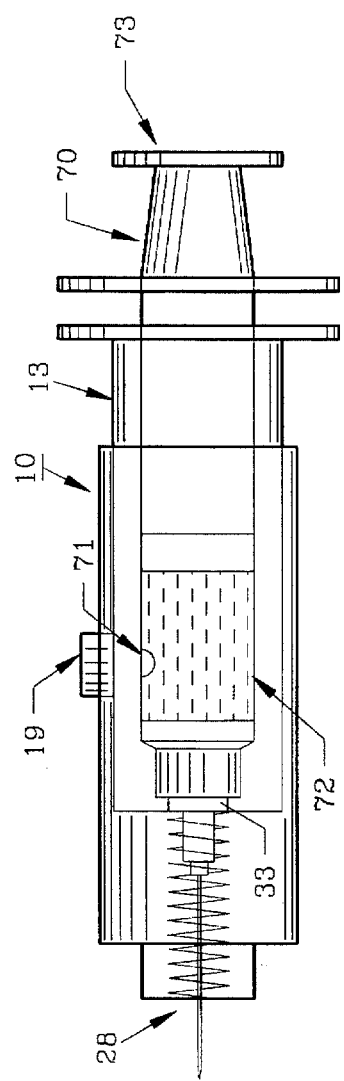
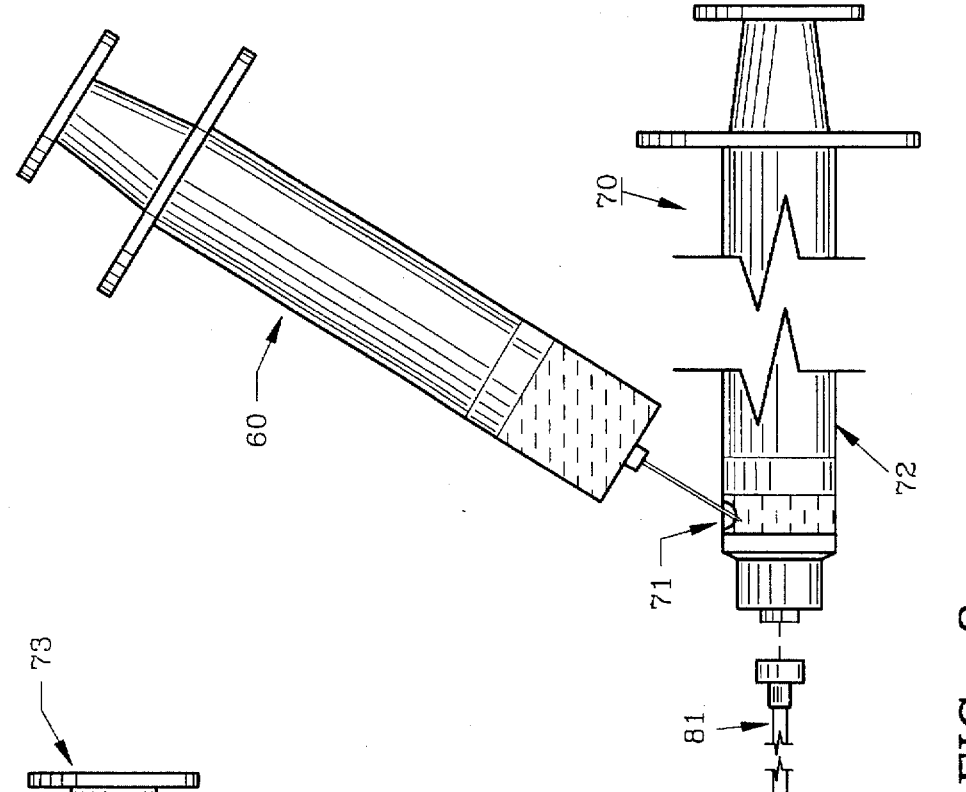
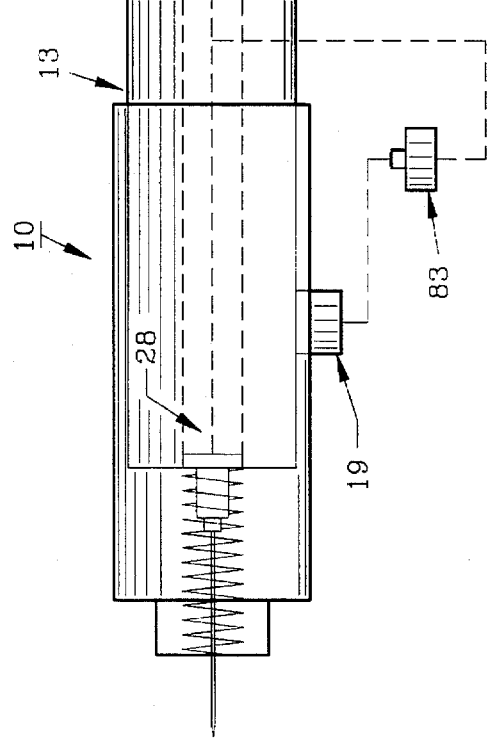
FIG. 7
FIG. 8

SYRINGE APPARATUS

FIELD OF THE INVENTION

The invention herein pertains to medical equipment and particularly to syringes and related apparatus for injecting and removing fluids from the human body. In one embodiment a syringe apparatus is provided which is multi-functional in that it can be used with conventional syringes, blood vials and IV equipment for a variety of purposes.

BACKGROUND AND OBJECTIVES OF THE INVENTION

In recent years medical equipment, services and devices have all escalated in price causing doctors, hospitals and others to pay very close attention to all medical supply and equipment purchases. More and more disposable equipment has been used for safety and sanitation purposes in recent years which also has adversely impacted the costs to a patient. Syringes are some of the most common devices used by medical practitioners and can be the most dangerous in spreading infectious diseases. Various types of covers, caps and shields have been conceived to help prevent accidental needle puncture from syringes, all with varying degrees of success. However, modifications made to standard syringes adds to the cost and such improvements must be carefully evaluated for effectiveness before they are adapted as a standard.

Thus, with the disadvantages and problems associated with prior art syringes, the present invention was conceived and one of its objectives is to provide a multi-purpose syringe apparatus which can be used for vaccinations, blood sampling, and IV solutions.

It is yet another objective of the present invention to provide a syringe which includes a penetrable member whereby additional fluids can injected therethrough.

It is also an objective of the present invention to provide a syringe apparatus which can be used with either a single pointed or double pointed needle.

Another objective of the present invention is to provide a syringe apparatus which includes a lockable and slidable inner sleeve with needle attached.

It is a further objective of the invention to provide a syringe apparatus in which the inner sleeve has a needle which is withdrawn by a resilient member to prevent accidental needle puncture when the plunger is released.

Various other objectives and advantages of the present invention will become apparent to those skilled in the art as a more detailed explanation is set forth below.

SUMMARY OF THE INVENTION

Syringe apparatus having multiple uses includes an outer cylindrical sleeve and an inner sleeve having a needle attached. A resilient member spring urges the inner sleeve and needle upwardly to maintain the needle interiorly of the outer sleeve when not in use to prevent accidental needle puncture. Conventional syringes can be inserted into the inner sleeve and attached to the needle for use in vaccinations and the like.

In the preferred embodiment the syringe apparatus has a double-pointed needle for use with a blood vial for blood collection and for other purposes. A C-shaped slot along the outer sleeve allows a projecting penetrable member on the inner sleeve to lock the sleeves together as required before or after use such as during an IV application. The penetrable member also allows fluids to be directed into the inner sleeve as needed without the necessity of removing the needle from the patient.

BRIEF DESCRIPTION OF THE DRAWINGS

The followings drawings are presented in somewhat schematic fashion to better illustrate the internal components as follows:

FIG. 1 shows the preferred form of the syringe apparatus of the invention in a locked position with the needle extended and the plunger removed therefrom;

FIG. 2 illustrates an end view of the syringe apparatus as shown in FIG. 1 along lines 2—2;

FIG. 3 depicts another end view of the syringe apparatus of FIG. 1 along lines 3—3;

FIG. 4 pictures an alternative embodiment of the syringe apparatus with a single pointed needle;

FIG. 5 pictures the syringe apparatus as shown in FIG. 1 with a conventional blood vial remove therefrom;

FIG. 6 demonstrates the syringe apparatus as seen in FIG. 4 with a conventional syringe removed therefrom;

FIG. 7 illustrates the syringe apparatus with a novel syringe affixed therein;

FIG. 8 shows the syringe apparatus of the invention with an IV apparatus and conventional syringe.

DESCRIPTION OF THE PREFERRED EMBODIMENT

Figure 9:
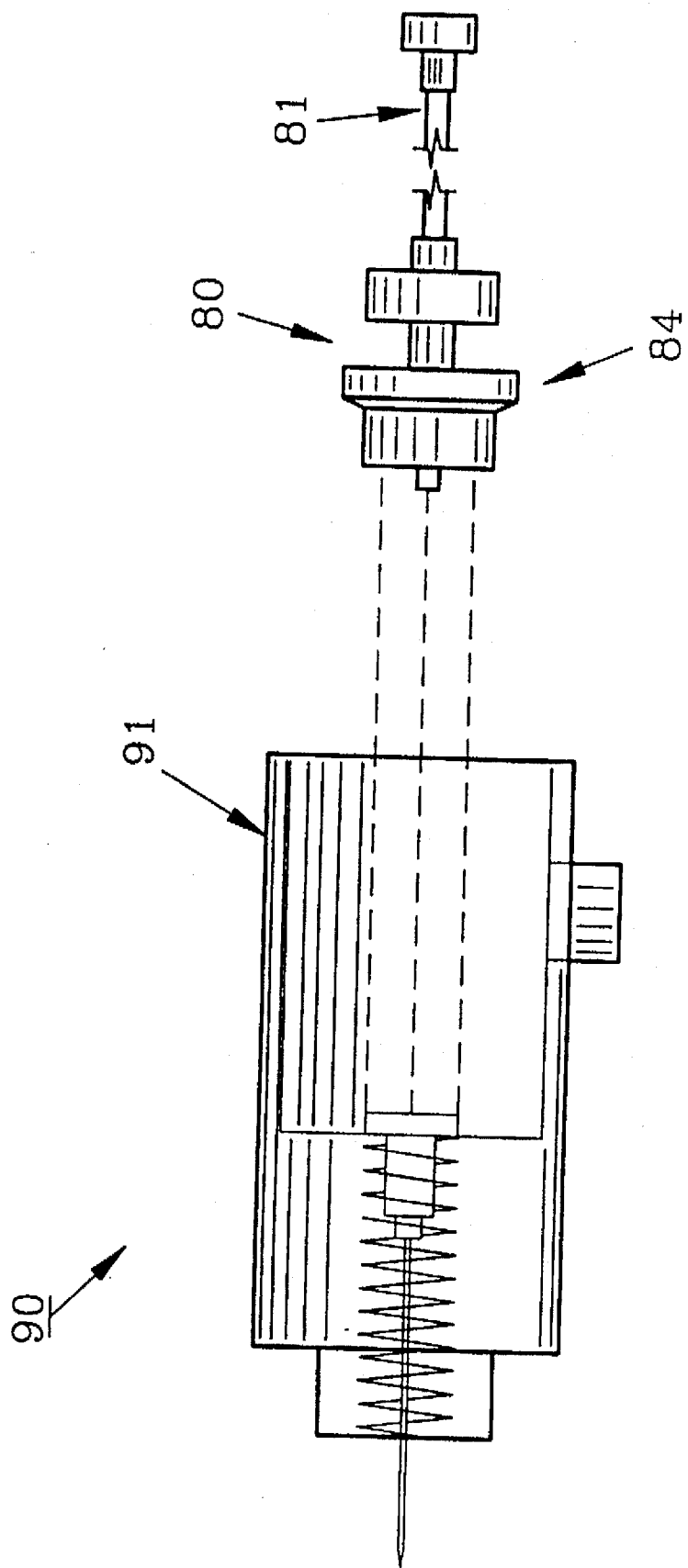
FIG. 9 features another syringe apparatus and certain of the IV components as shown in FIG. 8.

The preferred form of the invention is seen in FIGS. 1, 2 and 3 where the syringe apparatus is seen with the plunger removed therefrom. The apparatus includes a double-pointed needle and when used for usual injection purposes, the plunger, under manual pressure, forces fluid contained within the inner sleeve through the double needle and into the patient. A resilient member in the form of a coiled spring causes the double pointed needle to quickly withdraw within the outer sleeve to thus prevent accidental needle puncture when the device is not in use or prior to pressure being applied to the plunger. The plunger provides a receptacle for the interior end of the needle in the event additional fluids are utilized for injection or other purposes. A projecting penetrable member is positioned along the inner sleeve consisting of a resilient rubber or polymeric substance. This resilient substance will allow needle penetration but will seal when the penetrating needle is withdrawn as commonly used in the vaccine industry on various types of caps and bottles. The cylindrically-shaped projecting penetrable member has a second function as illustrated in FIG. 4 in that it allows the inner sleeve to be locked into position within the C-shaped slot of the outer sleeve. This locking arrangement allows the inner sleeve and outer sleeve to be releasably positioned one to the other, such as when using a plunger as shown in FIG. 1 for fluid injection into a patient. The C-shape slot including locking fingers along one end thereof.

The outer sleeve and inner sleeve shown in FIG. 4 are identical to the sleeves as shown in FIG. 1. However, as seen in the preferred embodiment of FIG. 1, a double-pointed needle is in place surrounded by a coiled spring. The alternate embodiment as shown in FIG. 4 has only a single pointed needle, likewise surrounded by a coiled spring. The preferred syringe apparatus of FIG. 1 can also be used with a blood vial as shown in FIG. 5 or can be used with an IV apparatus as shown in FIG. 8.

DETAILED DESCRIPTION OF THE INVENTION AND ITS OPERATION

For a better understanding of the invention and its uses, turning now to the drawings, FIG. 1 shows syringe apparatus 10 with plunger 11 removed therefrom. Syringe apparatus 10 includes an outer cylindrical sleeve 12 and a smaller diameter inner sleeve 13 slidably positioned within. Inner sleeve 13 has affixed at its terminal end 14 a double-pointed needle 15 which passes through distal end 16 of outer sleeve 12 as also shown in FIG. 2. Double-pointed needle 15 is conventional in the medical art and as shown, is surrounded by a coiled spring 17 which urges needle 15 inwardly, from left to right in FIG. 1 thereby fully retracting needle 15 through egress 37 within outer sleeve 12. In an alternate embodiment in FIG. 4, single-pointed needle 28 is withdrawn, and accidental puncture of the skin is thereby prevented, which provides a safety benefit to user. Outer sleeve 12 includes a C-shaped slot 18 (FIG. 4) which allows cylindrically-shaped penetrable member 19 to lock in place as required along outer sleeve 12 at one end of slot 18, a pair of locking fingers A retain penetrable member 19 in place with inner sleeve 13 extended from outer sleeve 12 as shown in FIG. 4. Finger A requires slight manual pressure to allow penetrable member 19 to pass through. In ordinary use, such as for injection purposes, projecting penetrable member 19 is not locked in place. However, when syringe apparatus 10 is used for blood collection with blood vial 40 as shown in FIG. 5, the dual purpose projecting penetrable member 19 will be locked into place within slot 18 as shown in FIG. 1 with needle 15 extended through egress 37.

As also shown in FIG. 1, plunger 11 includes distal end 20 formed from a somewhat resilient material such as a rubber and also has a relatively rigid shank 21 which may be formed from a plastic material. Distal end 20 defines receptacle 22 which extends into rigid shank 21 as shown therein. Receptacle 22 allows reception of needle 15 as plunger 11 is urged internally of inner sleeve 13 such as by the application of thumb pressure on proximal end 24 as when vaccinating a patient.

In use, penetrable member 19 is locked in position as seen in FIG. 1 in foot 25 of C-shaped slot 18 (see FIG. 4) and thereafter vaccination fluid can be placed within inner sleeve 13. Next, plunger 11 is inserted into open end 26 of inner sleeve 13 and the patient is then vaccinated as usual. Once the vaccination has been completed, inner sleeve 13 can be rotated thus allowing penetrable member 19 out of foot 25 of slot 18 whereby sleeve 13 then returns to its normal position with needle 15 fully retracted within outer sleeve 12 as seen in FIG. 4. Syringe apparatus 10 and plunger 11 can then be disposed in accordance with health and safety regulations. In FIG. 2 the exterior end of outer sleeve 12 is seen along line 2—2 of FIG. 1.

In the alternate embodiment of the invention as seen in FIG. 4, a single-pointed needle 28 is shown with plunger 30 withdrawn as would be used for vaccine injection. Plunger 30 includes distal end 31 with receptacle 32 which is sized to receive interior end 33 of needle 28, also seen in FIG. 3.

In FIG. 5 syringe apparatus 10 is shown with blood vial 40 for blood collection. In actual use, blood vial 40 is urged internally of inner sleeve 13 whereby needle 15 punctures seal 41 to allow blood to flow through needle 15 into blood vial 40. After the blood sample has been collected, vial 40 is removed from syringe apparatus 10 and is transported to a laboratory or other location for blood testing purposes.

Syringe 60 as shown in FIG. 6 illustrates a conventional syringe with the needle removed therefrom. Syringe apparatus 10 can be used conveniently with syringe 60 by inserting syringe 60 into inner sleeve 13 with end 33 of needle 28 threadably joined to distal end 61 of syringe 60 as is conventionally assembled. Thus, a typical syringe, such as syringe 60 can be used with syringe apparatus 10 with the safety feature of retractable needle 28 available.

FIG. 7 demonstrates syringe apparatus 10 having single-pointed needle 28 attached to syringe 70 at end 33. Syringe 70 includes a penetrable member 71 and is aligned within inner sleeve 13 to allow a needle to penetrate both penetrable member 19 on inner sleeve 13 and penetrable member 71 on syringe 70 to thereby allow fluid to be injected through syringe apparatus 10 and into syringe 70. Penetrable member 71 like penetrable member 19 consists of a resilient material. This feature allows additional fluid to be injected into a patient as needed without removal of needle 28 from the patient. In use, syringe 70 is affixed within inner sleeve 13 as shown at FIG. 7 with fluid to be injected within barrel 72. If the fluid volume contained within barrel 72 is determined inadequate, then additional fluid can then be injected through a needle directed through projecting penetrable member 19, penetrable member 71 and into barrel 72. Thereafter, plunger 73 can then be urged inwardly, causing the new supply of fluid to pass through needle 28 and on into the patient.

FIG. 8 depicts syringe apparatus 10 positioned with IV apparatus 80 shown in fragmented fashion for illustrative purposes. IV apparatus 80 is conventional in the art and IV tubing 81 may be ten or more feet long as needed. In use, IV apparatus 80 is attached to needle 28 within inner sleeve 13 and when fully assembled, syringe 70 which is filled with an appropriate solution is used to force said fluid into needle 28 which is in a patient. As further seen in FIG. 8, once the fluid within syringe 70 is exhausted, a conventional syringe 60 which is filled with the selected fluid can be used to supply syringe 70 with additional fluid by injection through penetrable member 71 as seen. Thus, syringe apparatus 10 allows fluid delivery through IV apparatus 80 as needed without the necessity of removing or replacing needle 28 from the patient's body. Penetrable member 19 may be substituted with fitting 83 which would join directly to IV coupler 84 for a conventional connection if desired.

In FIG. 9 another IV set-up is shown, with outer sleeve 91 of syringe apparatus 90 shortened to allow ease in connection with IV apparatus 80.

Various modifications and changes can be made to the invention by those skilled in the art and the examples herein are merely for explanatory purposes and are not intended to limit the scope of the appended claims.

We claim:

1. Syringe apparatus comprising: an outer sleeve, an inner sleeve, said inner sleeve slidably positioned within said outer sleeve, a penetrable projection, said penetrable projection attached to said inner sleeve, said outer sleeve including a slot, said penetrable projection receivable within said slot; a needle attached to said inner sleeve, said outer sleeve having a distal end defining a needle egress, a resilient member, said resilient member attached to said inner sleeve and to said outer sleeve distal end, said resilient member disposed between said inner and outer sleeves, said needle extendable from within said outer sleeve through said egress, and said needle retractable through said egress by said resilient member.

2. Syringe apparatus as claimed in claim 1 wherein said outer sleeve slot is a C-shaped locking slot.

3. Syringe apparatus as claimed in claim 2 wherein said locking slot comprises a foot.

4. Syringe apparatus as claimed in claim 1 and including a syringe, said syringe for positioning within said inner sleeve in fluid communication with said needle.

5. Syringe apparatus as claimed in claim 4 wherein said syringe comprises a fluid receptacle, a fluid receptacle penetrable member, said fluid receptacle penetrable member positioned on said fluid receptacle.

6. Syringe apparatus as claimed in claim 1 and including a plunger located within the inner sleeve, said plunger having a proximal end and a distal end, said distal end defining a needle receptacle.

7. Syringe apparatus as claimed in claim 6 wherein said needle receptacle is elongated.

8. Syringe apparatus as claimed in claim 1 and including a blood vial, said blood vial in fluid communication with said needle.

9. Syringe apparatus as claimed in claim 1 and including an IV assembly, said IV assembly for attachment to said needle.

10. Syringe apparatus as claimed in claim 1 wherein said needle comprises a dual pointed needle.

11. Syringe apparatus as claimed in claim 1 wherein said needle comprises a single pointed needle.

* * * * *